United States Patent [19]

Oppenheimer

[11] Patent Number: 5,601,080
[45] Date of Patent: Feb. 11, 1997

[54] SPECTROPHOTOMETRIC BLOOD ANALYSIS

[75] Inventor: Luis Oppenheimer, Winnipeg, Canada

[73] Assignee: Coretech Medical Technologies Corporation, Winnipeg, Canada

[21] Appl. No.: 365,033

[22] Filed: Dec. 28, 1994

[51] Int. Cl.⁶ ........................................ A61B 5/00
[52] U.S. Cl. .......................... 128/633; 128/664; 128/665; 356/39
[58] Field of Search ..................... 128/632, 633, 128/634, 635, 637, 664, 665, 666, 667; 356/39, 40, 41

[56] References Cited

U.S. PATENT DOCUMENTS

| H1114 | 12/1992 | Schweitzer et al. . | |
|---|---|---|---|
| 3,705,771 | 12/1972 | Friedman et al. | 356/39 |
| 3,830,569 | 8/1974 | Meric . | |
| 4,243,883 | 1/1981 | Schwarzmann . | |
| 4,484,135 | 11/1984 | Ishibara et al. . | |
| 4,515,165 | 5/1985 | Carroll . | |
| 4,735,504 | 4/1988 | Tycko . | |
| 4,745,279 | 5/1988 | Karkar et al. . | |
| 4,776,340 | 10/1988 | Moran et al. . | |
| 4,819,752 | 4/1989 | Zelin . | |
| 5,048,524 | 9/1991 | Bailey . | |
| 5,066,859 | 11/1991 | Karkar et al. . | |
| 5,149,503 | 9/1992 | Kohno et al. . | |
| 5,190,040 | 3/1993 | Aoyagi . | |
| 5,195,963 | 3/1993 | Yafuso et al. . | |
| 5,331,958 | 7/1994 | Oppenheimer . | |

OTHER PUBLICATIONS

Oppenheimer et al, *J. Appl. Physiol.*, 62(1): 364 (1987).
Oppenheimer et al, *J. Appl. Physiol.*, 69(2): 456 (1990).

Primary Examiner—Angela D. Sykes
Assistant Examiner—Eric F. Winakur
Attorney, Agent, or Firm—Timothy R. Kroboth

[57] ABSTRACT

A spectrophotometric method and device are described which are particularly useful for on-line monitoring and control of blood parameters. Determination of a blood parameter without measuring or directly following another blood parameter, is made possible by using information contained in scatter and at least three distinct detection locations. Calibration using means for scattering a light beam to a suitable reference geometry, is beneficially used. Constant values related to the detection locations are derived. Later, these constants may be used to determine a blood parameter. Two different wavelengths and at least for detectors may be used. The device is beneficially applied to extracorporeal circuits, and may be used to optimize dialysis.

18 Claims, 5 Drawing Sheets

SPECTROPHOTOMETRIC BLOOD ANALYSIS

BACKGROUND OF THE INVENTION

This invention relates to the spectrophotometric analysis of blood parameters.

Blood parameters or indices such as transvascular fluid exchange, provide important clinical information. For example, there are a number of clinical conditions, e.g. renal failure and massive fluid overload, which require fluid removal and in which it would be beneficial to be able to achieve an optimal rate of fluid removal.

Commonly used clinical approaches for fluid removal include an extracorporeal circuit. Because the body tissues and the blood stream are in direct communication, fluid removal from the blood results in an imbalance of forces which favors fluid movement from the tissues toward the blood stream. Continuous fluid removal from the blood stream therefore results in continuous mobilization from the tissues, which is the ultimate purpose of the therapy.

However, if fluid removal from the blood stream is induced at a rate faster than fluid can be mobilized from the tissues, patients can become hypotensive (shock). This complication is difficult to predict even if blood pressure is followed continuously. To prevent this possibility, fluid removal may be induced at a slow rate. However, it is desirable to achieve a maximal rate of fluid removal which can be matched safely by fluid mobilization from the tissues into the blood stream. In this way, dialysis may be optimized.

As illustrated by U.S. Pat. Nos. 3,830,569 to Meric, 4,243,883 to Schwartzmann, and 4,735,504 to Tycko, a spectrophotometric device for measuring blood indices including a suitable light source and photodetector is known. The light source may be a laser with a collimating lens mounted in front of the laser, and the light source may be remote from or proximate to the blood. As shown by Meric, multiple detectors in combination with a centrally disposed, light trap have been used, and a shield provided with windows may be disposed in the light path. Tycko processes forward scattered light by separating based upon high or low angular interval, prior to detection by separate detectors.

Also known as exemplified by U.S. Pat. No. 4,484,135 to Ishibara et al, is hematocrit determination by blood resistivity measurement. This patent criticizes measurements deriving hematocrit from blood cell count and mean blood cell volume, for using diluted blood if the concentration of the electrolyte and protein in the diluted blood has been changed.

As illustrated by *J. Appl. Physiol.*, 62(1): 364 (1987), light transmissive, plastic tubing through which blood is circulated, may be placed between light sources and light detectors disposed generally opposite from the light sources. As exemplified by *J. Appl. Physiol.*, 69(2): 456 (1990), to ensure detection of a widely scattered light beam, detectors connected in parallel to a photodetector circuit may be used. A separate detector may measure light fluctuations. Diluted perfusate is described.

Unless taken into account, measurement artifacts may induce error in determining blood parameters from optical properties of the blood. One well-known artifact results from changes in the degree of oxygen saturation of hemoglobin ($SaO_2$). This artifact may be avoided by selecting a specific wavelength or isobestic point at which the hemoglobin oxygen content does not influence light transmission. Isobestic points are known in the IR range (approximately 814 nm), in the green range (approximately 585 and 555 nm), and in the UV range.

As illustrated by U.S. Pat. Nos. 4,745,279 to Karkar et al, 4,776,340 to Moran et al, 5,048,524 to Bailey, 5,066,859 to Karkar et al, and 5,149,503 to Kohno et al, additional light sources or detectors have been used. Karkar '279 uses a detector for diffused light in combination with a compensating detector directly illuminated by another light source. Bailey uses a reference photocell to correct for variation in intensity of a light source, and describes a calibration fluid. Moran uses a catheter including a far detector and a near detector, and a non-linear equation based upon the near/far ratio to calculate hematocrit. Similar to Moran is Kohno, which describes an additional emitter location, and uses a non-linear equation based upon signal ratio to calculate hemoglobin.

Karkar '859 uses a pair of far field detectors and a pair of near field detectors. The far field detectors are spaced equidistant from a light emitting fiber, and one of the far field detectors is used to compensate for the signal detected by its paired fiber. A calibration procedure is described. Hematocrit measurement is compensated for the effects of oxygen saturation, pH and temperature. Karkar '859 points out that neither Karkar '279 nor Moran compensate for the effects of proteins and pH.

Despite the foregoing improvements in using the optical properties of blood to determine blood indices, further improvement is needed to provide a clinically useful methodology and device. Beneficially, monitoring of fluid removal would be made practical.

SUMMARY OF THE INVENTION

U.S. Pat. No. 5,331,958 is particularly focused in one aspect, on taking into account factors that influence change in light scatter, by for instance, compensating for change in light beam geometry induced by change in blood electrolyte composition, when optically determining a blood parameter such as hematocrit.

In accordance with the purpose of the present invention, as embodied and broadly described herein, there is provided a novel method for optically determining blood parameters. In accordance with the method, at least one light beam is directed into a patient's blood, and light emerging from the blood is detected and measured for the purpose of using scatter as a source of information.

In the present invention, it is beneficial to use either more than a single light source or more than two detectors. Because scatter is different at different wavelengths and scatter is being used as a source of information, the choice of a second wavelength or of even three of more wavelengths benefits this approach. Moreover, a second wavelength may be used to eliminate any oxygen saturation artifact.

Because scatter provides different information at different locations, the choice of three or more distinct detection locations likewise benefits this approach. As will become understood, four distinct detection locations may be provided by combinations including two spaced apart detectors and two light sources. As appropriate, more than four distinct detection locations may be used. Advantageously, suitable locations are selected for evaluating intensity and geometry of an emerging light beam, and one of the locations is predominantly sensitive to directly emerging light.

When a single light source is used, an isobestic IR wavelength, in particular a near infrared wavelength, is generally preferred. When two light sources are used, an IR wavelength in combination with a visible wavelength such as a red wavelength, is typically useful. When three light sources are used, it is typically advantageous for two wavelengths to be IR wavelengths, and for one wavelength to be an isobestic wavelength. As applied to transmitted light, the combination of an IR wavelength and a through detector is usually beneficial.

By the present invention, signal data obtained from detecting and measuring emerging light are correlated with independently measured data for a selected blood parameter. To provide for the correlation, the signal data and measured data are beneficially substantially simultaneous in time. Advantageously, a plurality of constant values are derived from the correlation, for use in subsequently determining the selected blood parameter at a later time. Thereafter, signal data obtained from detecting and measuring emerging light at a later point in time, and derived constant values are used to determine a value of the selected blood parameter at the later point in time. Beneficially, intensity and geometry of an emerging light beam are detected and measured.

Advantageously, in making the determination, wavelength/detector location combinations that provide useful data are selected, and any wavelength/detector location combination that provides insignificant data or data that do not contribute positively to the determination, may be disregarded. In one approach, the determination may make use of the intensity of emerging light of one wavelength at a first distinct detection location, the intensity of emerging light of a second wavelength at a second distinct detection location, and the intensity of emerging light of a third wavelength at a third distinct detection location. In another approach, the determination may make use of the intensity of emerging light of one wavelength at a first distinct location, the intensity of emerging light of the same wavelength at a second distinct location, and a ratio of the intensities.

In regard to the prior approach of compensating for change in light beam geometry, endogenous macromolecules such as protein, have an effect on scatter. By comparison, by the present invention, a selected blood parameter may be determined using information contained in scatter, independently of measuring or specifically following another blood parameter. Thus, hematocrit may be determined independently of specifically following protein or electrolyte concentration, and concentration of endogenous, optically detectable macromolecules, hemoglobin concentration, electrolyte concentration, $pO_2$, pH and oxygen saturation may be determined independently, and so forth. Furthermore, other blood parameters such as blood oxygen content, may be calculated based thereon. The term "blood parameter" as used in this description, includes blood concentration not only of endogenous macromolecules but also of exogenous, optically detectable macromolecules.

In the present invention, it is beneficial to calibrate using means for scattering a light beam to a suitable reference geometry. Calibration is achieved by assigning a selected value to emerging light sensed at each distinctly located detector.

Also provided is a novel device for optically determining blood parameters. As indicated, in one embodiment, the device advantageously includes four distinct detection locations. When two light sources are used, two detectors spaced apart from each other may provide four distinct detection locations. More specifically, two detectors may serve as near and far locations with respect to one light beam, and with respect to the other light beam, one detector may serve to predominantly detect directly emerging light and the other detector may serve as a scatter detection location. Two light sources and four detectors may be similarly used. When one light source is used, four detectors spaced apart from one another, may be similarly used to provide four distinct detection locations, one of which as applied to transmitted light, may be a through detector location.

In another embodiment, the device advantageously includes at least three distinct detection locations for evaluating emerging light. In this case, three light sources may be used, each with its respective detector. Advantageously, one detector may serve to predominantly detect directly emerging light, and the other detectors may serve as scatter detectors.

Beneficially, a device in accordance with the present invention, may be used with an extracorporeal circuit through which blood flows, to continuously or intermittently monitor a patient for selected blood parameters, including circulating blood volume. Change in circulating blood volume may be advantageously monitored based upon hemoglobin concentration as optically determined in accordance with the present invention. This information may be beneficially used for fluid management, for instance, to regulate the rate of fluid removal.

In the drawing and in the detailed description of the invention that follows, there are shown and essentially described only preferred embodiments of this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

DETAILED DESCRIPTION OF THE INVENTION

When a light beam is directed into blood, the intensity and geometry of the emerging light is determined by the extent of absorption and the degree of scatter. Incident light is significantly scattered by a red cell suspension so that a significant fraction (scattered fraction) is no longer generally perpendicular when it reaches a detecting surface. This phenomenon influences not only the fraction of light which reaches a particular detecting surface, but also the degree of scatter, and hence the current generated by a photodetector for any given incident light. In hemolyzed blood, scatter will be negligible.

Figure 1:
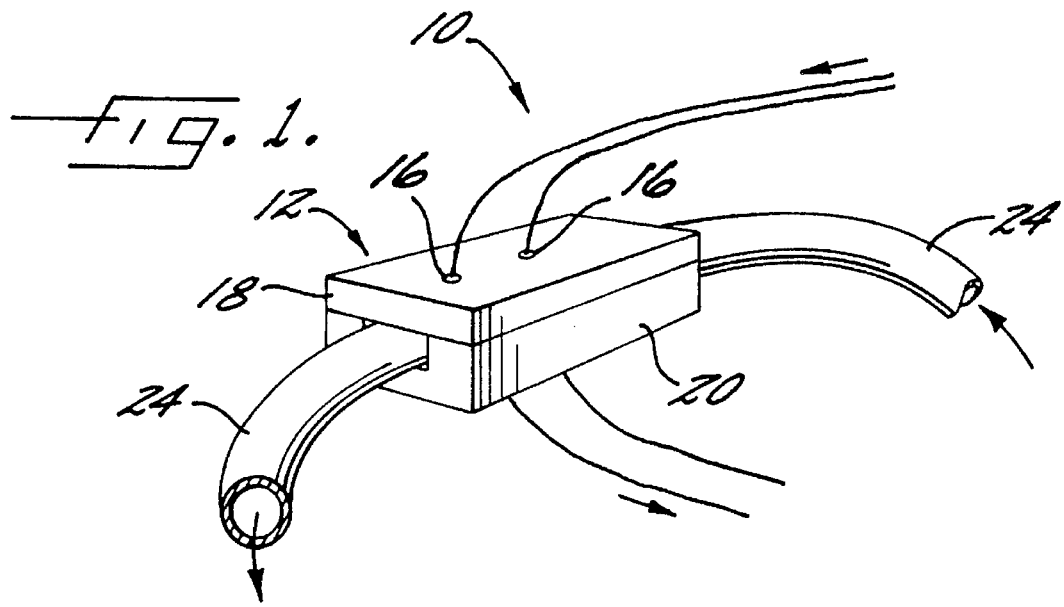
FIG. 1 is a perspective view of a portion of a preferred analysis device in accordance with the present invention.
Figure 2:
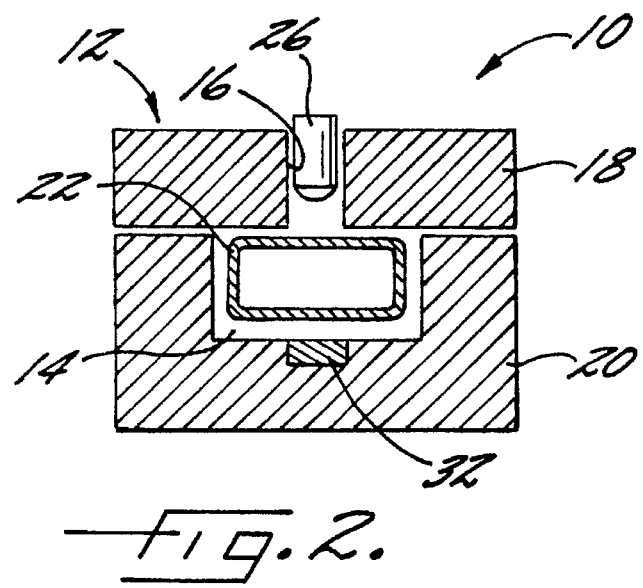
FIG. 2 an enlarged cross-sectional view of the device shown in FIG. 1.
Figure 3:
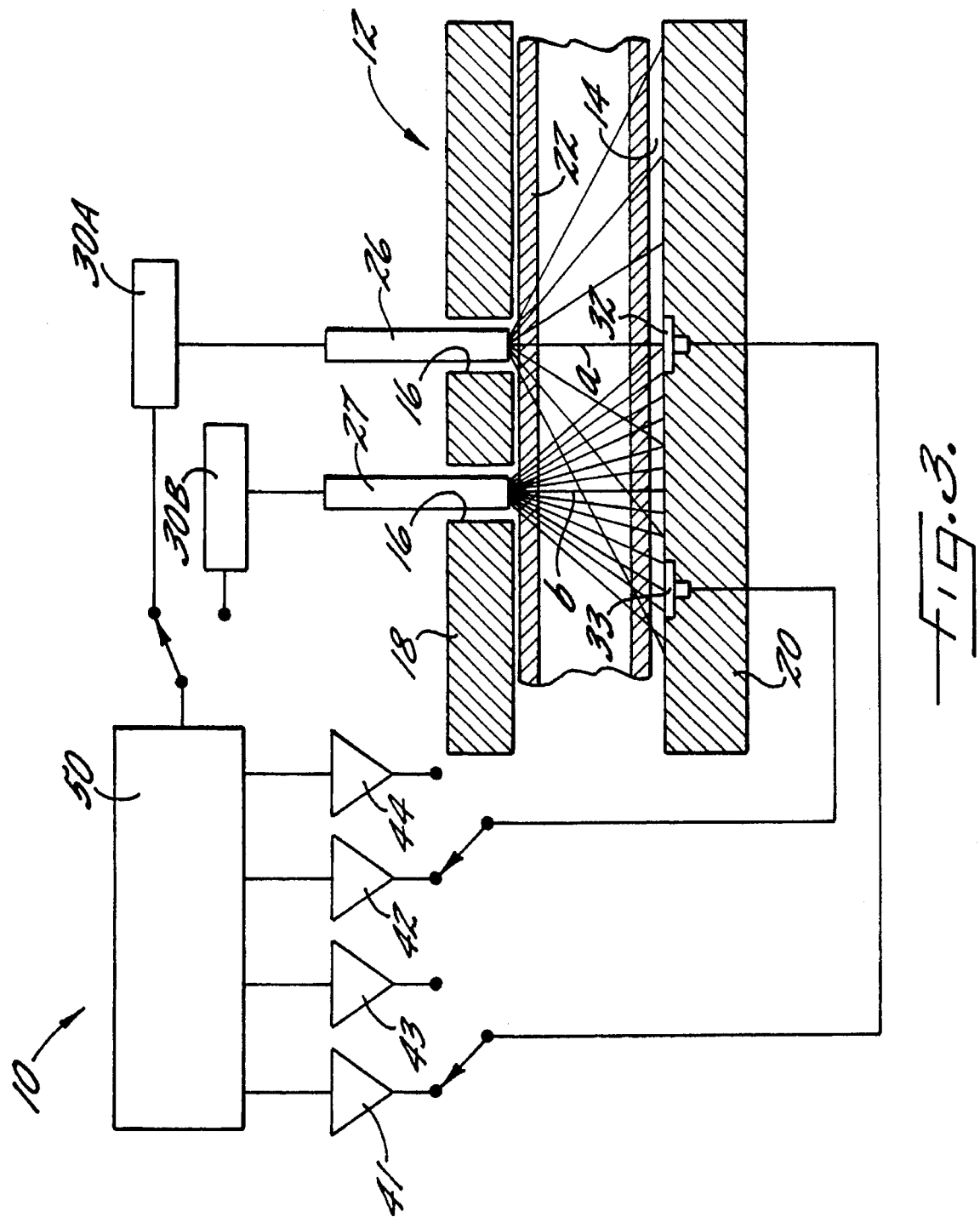
FIG. 3 is a schematic diagram of the device of FIG. 1.

In accordance with the present invention, a device 10 is provided in the preferred embodiment shown in FIGS. 1 to 3. Beneficially, there is no need to carry out prior to analysis, artificial intervention by which a patient's blood is diluted, or the blood is hemolyzed, or, as described in U.S. Pat. Nos. 3,830,569 to Meric and 4,735,504 to Tycko, the red cells are spherized. Rather, the present invention may be advantageously applied to circulating blood within an extracorporeal circuit, without detrimental effect on the blood.

Made of opaque plastic, housing 12 includes a channel 14 for receiving a light transmissive, flow cell 22, which has extracorporeal circuit tubing 24 attached to each end. In accordance with the invention, device 10 includes means 26,27 for generating light beams, which may be the same or different wavelengths. Conventional drivers 30A,30B for each light source may be suitably used.

Beneficially, a light source that emits an isobestic wavelength, is used. A useful isobestic wavelength in the IR range, is approximately 815 nm. Other useful wavelengths include 940 nm (IR) and 670 nm (red). 940 nm is advantageous due to its particular sensitivity to water. A beneficial combination is an isobestic IR wavelength and a red wavelength, for instance, 815 nm and 670 nm.

Lasers are highly advantageous light sources. Other light sources include laserdiodes, LEDs and incandescent light sources. Like lasers, laserdiodes beneficially emit virtually a single wavelength. Incandescent light sources directed across narrow band width interference filters, may be used.

Suitably, each light source is disposed in a cylindrical opening 16 in a cover 18 of opaque plastic housing 12. The cylindrical openings serve to collimate the light beams. Alternatively, light sources 26,27 may be disposed remote from the housing. In this case, fiber optic cable carrying specific light, may be used.

In accordance with the present invention, device 10 includes detector means for detecting light emerging from the blood. These detector means are positioned at suitable locations for sensitivity to the intensity and geometry of the emerging light. Conventional photodiodes may be used. Importantly, light detector means 32,33 are disposed at different locations with respect to each light beam. The areas illuminated by light sources 26,27 are represented in FIG. 3, and indicate transmitted and scattered light for each beam of light.

Light detection means 32 is beneficially located so as to predominantly be sensitive to directly emerging light, that is, with light that maintains a generally straight-line path through the blood. To this end, as applied to transmitted light as shown in FIG. 3, detector 32 is directly illuminated by light source 26, and may be located in the center of the light beam, that is, in line with optical axis "a". Advantageously, in the case of through detector 32, the blood path length of directly transmitted light, is typically about 3 mm or more.

Light detection means 33 is located so as to be sensitive to emerging light that has been scattered, and for convenience, may be termed a "side detector". Beneficially, detectors 32,33 are spaced apart but located proximate to one another. An appropriate spacing depends upon factors including the length of the light path. For example, the spacing will be greater than the light path, and the spacing will be sufficient so that information from one detector differs from information from another detector. A spacing of about 1 cm, center to center, provides advantageous resolution for a light path of about 3 mm; too close a spacing as in the prior art catheter of Moran, should be avoided.

Conveniently, as applied to transmitted light, the detectors are located within an opposite side 20 of the housing from the light sources and situated so as to be adjacent the flow cell. Suitable dimensions for the detectors are about 4 mm×5 mm.

Of significance in the present invention is the location of the second light source. Advantageously, neither detector is directly illuminated by light source 27. Rather, optical axis "b" of a light beam from the second light source is spaced apart from the optical axis of the first light beam, and projects between detectors 32,33. Thus, detector 33 is not a "through detector" for light source 27. Moreover, light source 27 is offset so that optical axis "b" is closer to one detector than to the other. With reference to FIG. 3, light source 27 is advantageously located relatively closer to detector 33 than to detector 32, and thus, with respect to light source 27, detector 33 may be termed a "near detector" and detector 32 may be termed a "far detector". Suitably, light source 27 may be located, center to center, a distance of about 0.4 cm from detector 33, and a distance of about 0.6 cm from detector 32, using optical axis "b" as the center.

In this way, when two pulsed light sources are used, two detectors may provide four distinct detection locations. By comparison, if detectors 32,33 were equidistant from optical axis "b", there would not be four distinct locations. Beneficially, when 815 nm and 670 nm light sources are used, light detector 32 may be located so as to be sensitive to directly emerging light emanating from the 815 nm light source; and the 670 light source may be located so that light detector 32 is a "far detector" and light detector 33 is a "near detector".

As shown in FIG. 2, flow cell 22 is beneficially shaped to generally conform to the geometry of channel 14. If desired, light transmissive tubing inserted into extracorporeal circuit tubing 24, may be used in place of the flow cell, and the tubing may be conformed to the channel geometry upon the closing of cover 18.

In accordance with the present invention, and with particular reference to FIG. 3, device 10 further includes signal amplification means. Suitably, conventional operational amplifiers may be used. Advantageously, a first amplification means 41 operatively communicates with detector 32, and a second amplification means 42 operatively communicates with detector 33. Subsequently and as appropriate, a third amplification means 43 operatively communicates with detector 32, and a fourth amplification means 44 operatively communicates with detector 33. Detected signals from optically distinct locations are separately amplified.

Also in accordance with the present invention, the device advantageously includes conventional analog to digital (A/D) converter means and signal processing means 50. Conveniently, the A/D converter means includes four channels for separately processing the four incoming signals, for feeding to the signal processing means. The signal processing means operatively communicates with, and serves to separately evaluate the signals received from, the individual amplification means. A conventional microprocessor may be used as the signal processing means. Switching between a detector and particular amplification means may be suitably provided by conventional switch means for controlling signal feed from the detectors, and may be conveniently controlled by the microprocessor.

The microprocessor advantageously controls emission by light sources 26,27, via drivers 30A,30B. More particularly, in device 10, the light sources are pulsed sequentially, preferably using stable current supplies. Switching between drivers may be conveniently controlled by the microprocessor, and is beneficially coordinated with detector/amplification means switching. Photodetector signals, proportional to incident light, are processed by the microprocessor, which beneficially functions to use signal information to determine blood parameters of interest.

If desired, as earlier mentioned, light sources 26,27 may be remotely located from housing 12. In this case, each light beam may be split so as to be directed partially toward housing 12 and partially toward a second housing provided with a reference flow cell containing a standard. The second housing may be conveniently structured in like manner as housing 12, and will preferably include a pair of light sources and a pair of detectors located in identical manner as light sources 26,27 and detectors 32,33, and will be appropriately connected to the described circuitry. Signals from this reference flow cell may be processed in a similar manner as described in U.S. Pat. No. 5,331,958 for detectors 32,33 thereof. Use of a second housing permits calibration readings under the control of the microprocessor without removal of flow cell 22 from housing 12.

In the device shown, an operator removes flow cell 22 from housing 12 and inserts the reference flow cell. In this case, inaccuracy resulting from variability in or in aging of the detectors, will be avoided, and greater reliability should result. In either case, a calibrating standard for assigning a selected value to emerging light sensed at detector 32 and a selected value to emerging light sensed at detector 33, is beneficial.

Figure 7:
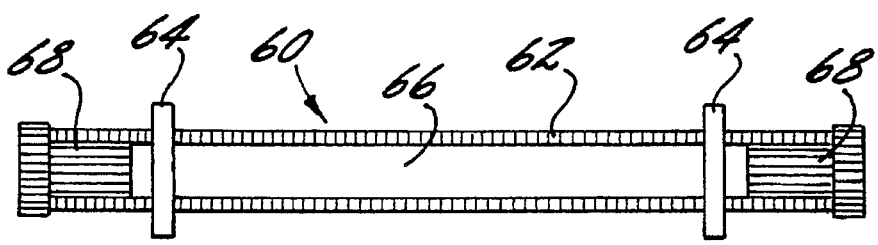
FIG. 7 is a cross-sectional view of a calibration means useful in the present invention.

In accordance with the invention and with reference to FIG. 7, calibration means 60 for scattering a light beam to a suitable reference geometry, is advantageously used. The reference geometry may differ from that of blood.

A useful calibrating standard is provided by a light transmissive, flow cell 62 having elements 64 corresponding to grooves in housing 12, filled with a suitable calibrating matrix 66, and sealed at its ends using plugs 68. Particles having a particle size in the range of about 1 micron to 1 mm, preferably about 3 to 100 microns, very preferably about 5 to 10 microns, form matrix 66. An appropriate particle size for a particular reference geometry depends upon factors including the length of the light path, because particle size and length of light path influence the degree of scatter. Generally speaking, to obtain a given degree of scatter, a relatively longer light path permits the use of relatively smaller particle size, whereas a relatively shorter light path will require the use of relatively larger particle size. Beneficially, the matrix particles are three-dimensionally fixed in their respective positions.

Depending upon the particle size, the calibrating matrix may require a light-absorbing additive to prevent saturation of the detectors. Thus, if particles of about 1 mm were used, such an additive may not be necessary; whereas particles of about 5 microns would typically require the additive. A suitable dye and/or colorant for use as a light-absorbing additive, is stable under the conditions of use, will selectively absorb light, and will be optimized to the light wavelengths to be used. Typically, the absorption will be in the visible and near infrared spectrum. Exemplary useful additives include copper phthalocyanine, indocyanine green, naphthol green B, prussian blue, and nigrosin.

A suitable matrix will not be opaque, but rather is substantially transmissive to light. Conveniently, matrix 66 may be provided by a homogeneous mixture of a silicone lubricant and a suitable additive or additives. In this case, the lubricant will be of sufficient viscosity under the conditions of use, to maintain a homogeneous mixture. Exemplary is a silicone lubricant available as Dow Corning Product #111. By comparison, a clear liquid such as the saline solution of Bailey, would not be useful in the present invention, because little scatter would be produced.

As may be understood, a useful calibrating standard may be prepared by mixing a suitable additive and matrix to provide a homogeneous mixture, charging the flow cell with the mixture, and sealing the filled flow cell. A small amount of additive is used in proportion to the matrix, and as indicated, is sufficient to prevent saturation of the detectors. For example, when the additive is copper phthalocyanine and the matrix is silicone lubricant, about 10 mg of additive may be conveniently mixed with about 4 gm of the matrix.

In accordance with the present invention, a method for determining blood parameters from optical properties of blood by using information contained in scatter, is provided. By the method, at least one light beam is advantageously directed into a patient's circulating blood, and light emerging from the blood is detected and measured using three or more distinct detection locations. As applied to transmitted light, the detection units may consist of through detector 32, and at an optically distinct location suitable for sensitivity to intensity and geometry of an emerging light beam, side detector 33; however, other elements or procedures useful for providing signals capable of enabling evaluation of the intensity and geometry of an emerging light beam, may be used.

In a preferred embodiment, calibration means 60 is placed into housing 12, the light sources are pulsed directing each light beam into the calibrating means, and a selected value is assigned to the emerging light detected and measured at each distinctly located detector. Thereafter, signal data are accumulated over a selected period of time using device 10, and independently measured data for a blood parameter or parameters of interest are obtained. The signal data and measured data are beneficially obtained substantially simultaneous in time. Based thereon, an appropriate equation including derived constant values, may be determined. By thereafter obtaining signal data at a subsequent point in time using device 10, and using the resultant signal information for solving the equation, the value of the blood parameter or parameters of interest at that subsequent point in time, may be determined independently of other blood parameters. As previously described, detector signals are separately amplified, and amplified signals are separately received by the signal processing means. Calibration may be at the outset and thereafter as appropriate.

With continued reference to device 10 of FIGS. 1 to 3, processing of signal information to determine a blood parameter (BP) of interest may use an equation that follows intensity and geometry of an emerging light beam, and that includes total intensity and a ratio of intensities. Illustrative is the following equation for wavelengths of 815 nm and 670 nm:

$$BP = A\log815TH + B\log815SD + C(\log815TH \times \log815SD) + D(\log815TH/\log815SD) + E\log670NR + F\log670FR + G(\log670NR \times \log670FR) + H(\log670NR/\log670FR) + I,$$

where 815TH is the signal from through detector 32, 815SD is the signal from side detector 33, 670NR is the signal from near detector 33, 670FR is the signal from far detector 32, and A, B, C . . . I are constants. As may be understood, this equation would be the same for other wavelengths except that the equation may specify the other wavelengths used. Total intensity could be evaluated by a sum of logs, rather than, as shown, a product of logs. In addition, the determination may not necessarily always require log calculations, and may even use a combination of logs and raw numbers.

By the present invention, multiple regression analysis is advantageously used to derive the constants A, B, C . . . I from the data accumulated over the selected period of time using device 10, and from the measured data for the blood parameter of interest. As may also be understood, the constants will likely vary depending upon the blood parameter of interest.

Evaluation is advantageously used to find components of the equation that either contribute insignificantly or do not contribute positively to the determination. Such components may be disregarded in selecting an appropriate equation. Variation in useful components of an equation may be expected depending upon factors including the blood parameter of interest and the wavelength or wavelengths used.

Even so, it should be noted that the foregoing equation beneficially includes data for intensity of emerging light of one wavelength detected at a first distinct detection location, data for intensity of emerging light of the same wavelength detected at a second distinct detection location, data for total intensity, and data for a ratio of the intensities. Advantageously, ratio data particularly inform as to the light beam geometry. However, as may be understood, it may not be necessary that an equation specify ratio data for emerging light beam geometry to be evaluated.

Because intermittent and continuous forms of dialysis including continuous hemofiltration, require an extracorporeal circuit, device 10 may be used on-line to continuously or intermittently monitor blood parameters by measuring light transmission changes across the circuit tubing or a flow cell inserted into the circuit. By monitoring a parameter such as hemoglobin, the rate of ultrafiltration may be optimized by providing for the maximum rate of fluid removal which will not result in a sustained or excessive increase in hemoglobin, that is, the maximal rate of fluid removal which can be matched safely by fluid mobilization from the tissues into the blood stream. Hemoglobin concentration may be a better index of circulating blood volume than hematocrit, because hematocrit can be influenced by the mean corpuscular volume.

Figure 4:
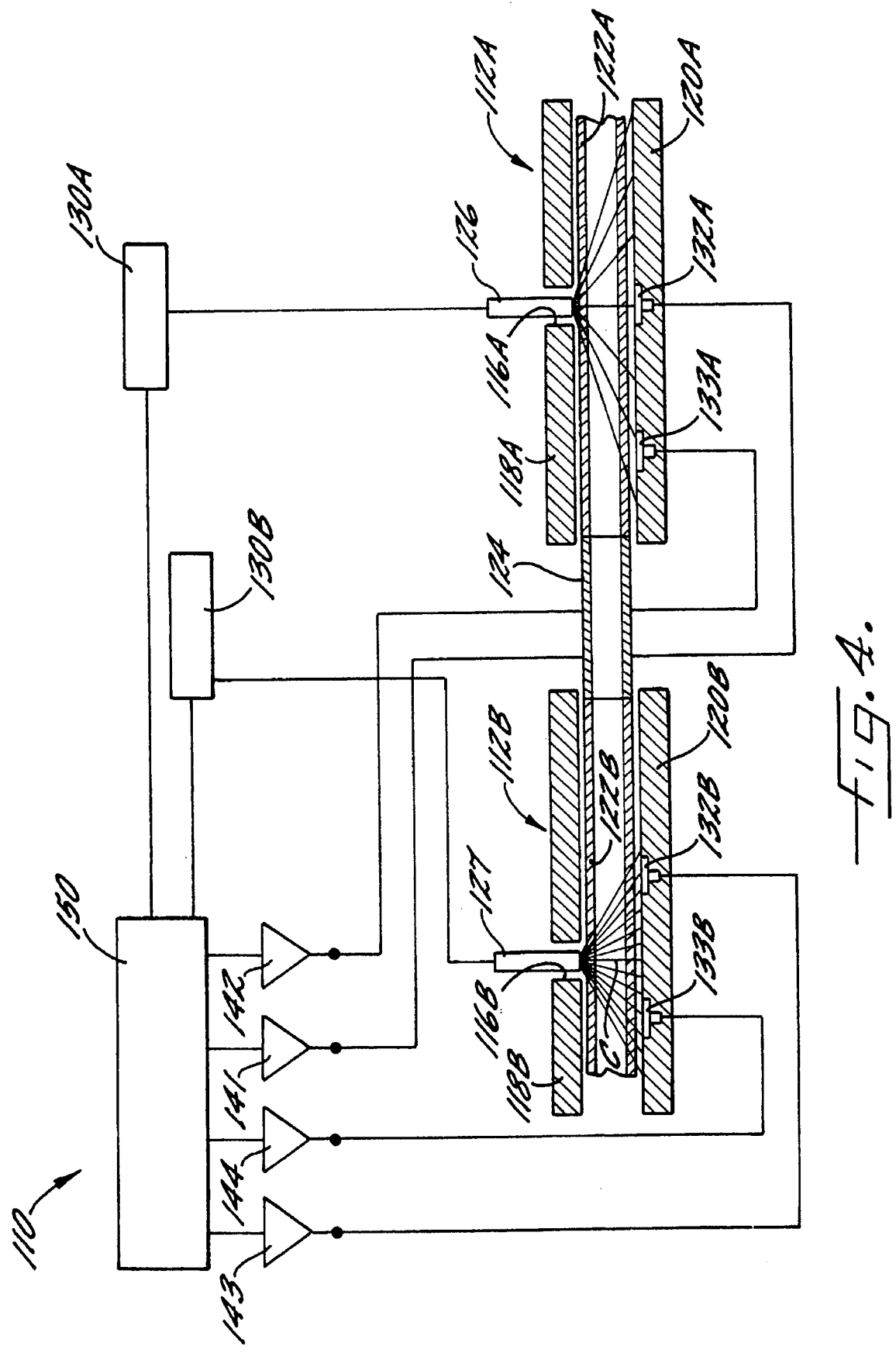
FIG. 4 is a schematic diagram of a second preferred analysis device in accordance with the present invention.

With reference to FIG. 4, a second preferred embodiment of the present invention is shown, in which to avoid the use of pulsed light sources, each light source is followed by separate detectors. Corresponding numerals are used in FIG. 4 to indicate parts of device 110 corresponding to device 10, and, for sake of brevity, no description is given of corresponding parts except as otherwise now provided.

In accordance with this embodiment, device 110 includes flow cells 122A,122B disposed within housings 112A,112B, extracorporeal circuit tubing 124 connecting the flow cells, and means 126,127 for generating light beams and detecting means 132A,133A,132B,133B disposed within the respective housings. Driver 130A drives the first light source, and driver 130B drives the second light source. The areas illuminated by the light sources are represented in FIG. 4, and indicate transmitted and scattered light for each beam of light.

As shown, each flow cell has a single light source and a separate set of detectors. Advantageously, the detectors within a set may be spaced apart, center to center, a distance of about 1 cm. Beneficially, one detector may be located so as to predominantly be sensitive to directly emerging light, and no other detector is directly illuminated by a light source. Optical axis "c" of a light beam from light source 127 projects between detectors 132B,133B. Moreover, light source 127 is offset so that the optical axis is closer to one detector than to the other.

In this way, four distinct detection locations are provided. When 815 nm and 670 nm light sources are used, detector 132A may be located to be predominantly sensitive to directly emerging light emanating from the 815 nm light source; and the 670 nm light source may be located so that detector 132B is a "far detector" and detector 133B is a "near detector".

In accordance with this embodiment, advantageously, a first amplification means 141 operatively communicates with detector 132A, a second amplification means 142 operatively communicates with detector 133A, a third amplification means 143 operatively communicates with detector 132B, and a fourth amplification means 144 operatively communicates with detector 133B. Also in accordance with this embodiment, the device suitably includes conventional analog to digital (A/D) converter means and signal processing means 150. Conveniently, the A/D converter means includes four channels for separately processing the signals.

In accordance with the present invention, device 110 of FIG. 4, constructed as shown and described, and comprising a 815 nm laser light source and detectors 132A,133A disposed in housing 112A and spaced apart, center to center, a distance of 1 cm, and having a 3 mm light path; and comprising a 670 nm laser light source and detectors 132B, 133B disposed in housing 112B and respectively spaced from optical axis "c" of the light beam a distance of 0.6 cm and 0.4 cm, is used to derive appropriate constants for determining hematocrit and $pO_2$, using the following equation:

$$BP = A\log815TH + B\log815SD + C(\log815TH \times \log815SD) + D(\log815TH/\log815SD) + E\log670NR + F\log670FR + G(\log670NR \times \log670FR) + H(\log670NR/\log670FR) + I,$$

where BP is hematocrit or $pO_2$, and the remaining components of the equation are as previously described. The detectors are 4 mm×5 mm in size.

A sealed flow cell containing a homogeneous mixture of copper phthalocyanine and silicone lubricant, is used as the calibration standard. Thereafter, signal data are obtained for circulating blood, and measured data for hematocrit and $pO_2$ are obtained.

The experimental design is as follows: each day over an eight day period, a circuit including flow cells 122A,122B is charged with approximately 250 ml fresh blood. The flow cells are respectively disposed in housings 112A,112B. Subsequently, four 15 ml volumes of plasma are added to the circuit at appropriate intervals. Then, four 400 microliter volumes of 3M sodium chloride are added to the circuit at appropriate intervals. Then, four 15 ml volumes of ultrafiltrate are removed from the circuit at appropriate intervals. Then, four 15 ml volumes of ultrafiltrate are added to the circuit at appropriate intervals. Oxygen tension is varied by changing the % $O_2$ in contact with the blood. Signal data are obtained using device 110 to monitor the foregoing interventions, and simultaneously measured data for hematocrit and $pO_2$ are obtained. Hematocrit is measured using a standard microhematocrit technique and an electrode measurement is used for $pO_2$. Each day over the eight day period, this experimental protocol is followed. As may be understood, this protocol results in the collection of signal data for hematocrit, while macromolecular (in particular protein) concentration and sodium concentration are changed in the circulating blood.

Thereafter, using multiple regression analysis, the accumulated signal data are correlated with the accumulated measured data for each of hematocrit and $pO_2$, and the constants and other pertinent information are derived, as shown in Table 1, for each of hematocrit and 233B is a "near detector" and detector 232B is a "far detector".

Advantageously, detectors 232A,233A are spaced apart, center to center, a distance "d1" of about 1 cm, and detectors 233B,232B are likewise spaced apart, center to center, a

TABLE 1

| HEMATOCRIT | Regression Output: | | | | | | | |
|---|---|---|---|---|---|---|---|---|
| Constant | 80.69418 | | | | | | | |
| Std Err of Y Est | 1.127662 | | | | | | | |
| R Squared | 0.948452 | | | | | | | |
| No. of Observations | 112 | | | | | | | |
| Degrees of Freedom | 103 | | | | | | | |
| X Coefficient(s) | −189.094 | 39.38935 | 83.83537 | 100.6733 | 33.77299 | −122.521 | 56.84819 | −52.7963 |
| Std Err of Coef. | 70.39295 | 24.46726 | 31.21500 | 34.87591 | 113.3110 | 11.80528 | 61.20441 | 50.14065 |
| $pO_2$ | Regression Output: | | | | | | | |
| Constant | 420.4210 | | | | | | | |
| Std Err of Y Est | 8.990607 | | | | | | | |
| R Squared | 0.788509 | | | | | | | |
| No. of Observations | 112 | | | | | | | |
| Degrees of Freedom | 103 | | | | | | | |
| X Coefficient(s) | 381.4914 | −218.026 | 87.66489 | −218.118 | −2370.38 | −339.712 | 1449.872 | 951.8296 |
| Std Err of Coef. | 561.2279 | 195.0722 | 248.8705 | 278.0581 | 903.4049 | 94.12101 | 487.9695 | 399.7606 |

$pO_2$. With reference to the Table, constants A, B, C . . . H are the "X Coefficient(s)" in the order shown, and constant I is the "Constant". Thereafter, at a subsequent point in time, signal data are obtained and the resultant information is used to solve the equation, to determine hematocrit and $pO_2$ at that subsequent point in time.

As may be understood, hematocrit is determined independently of specifically following or measuring protein or sodium concentration. Moreover, by comparison, the device of FIG. 4 of U.S. Pat. No. 5,331,958 will generally produce less accurate results. The combination of one light source and two detectors provides comparatively less information as to change in intensity and geometry of the emerging light beam.

Furthermore, using the approach of the present invention, hemoglobin or protein may be determined independently of measuring or specifically following hematocrit or sodium concentration. Applications include determination of blood concentration of additional hemoglobin species. To this end, wavelengths appropriate for optical detection of these species including carboxyhemoglobin and methemoglobin, may be used.

Figure 5:
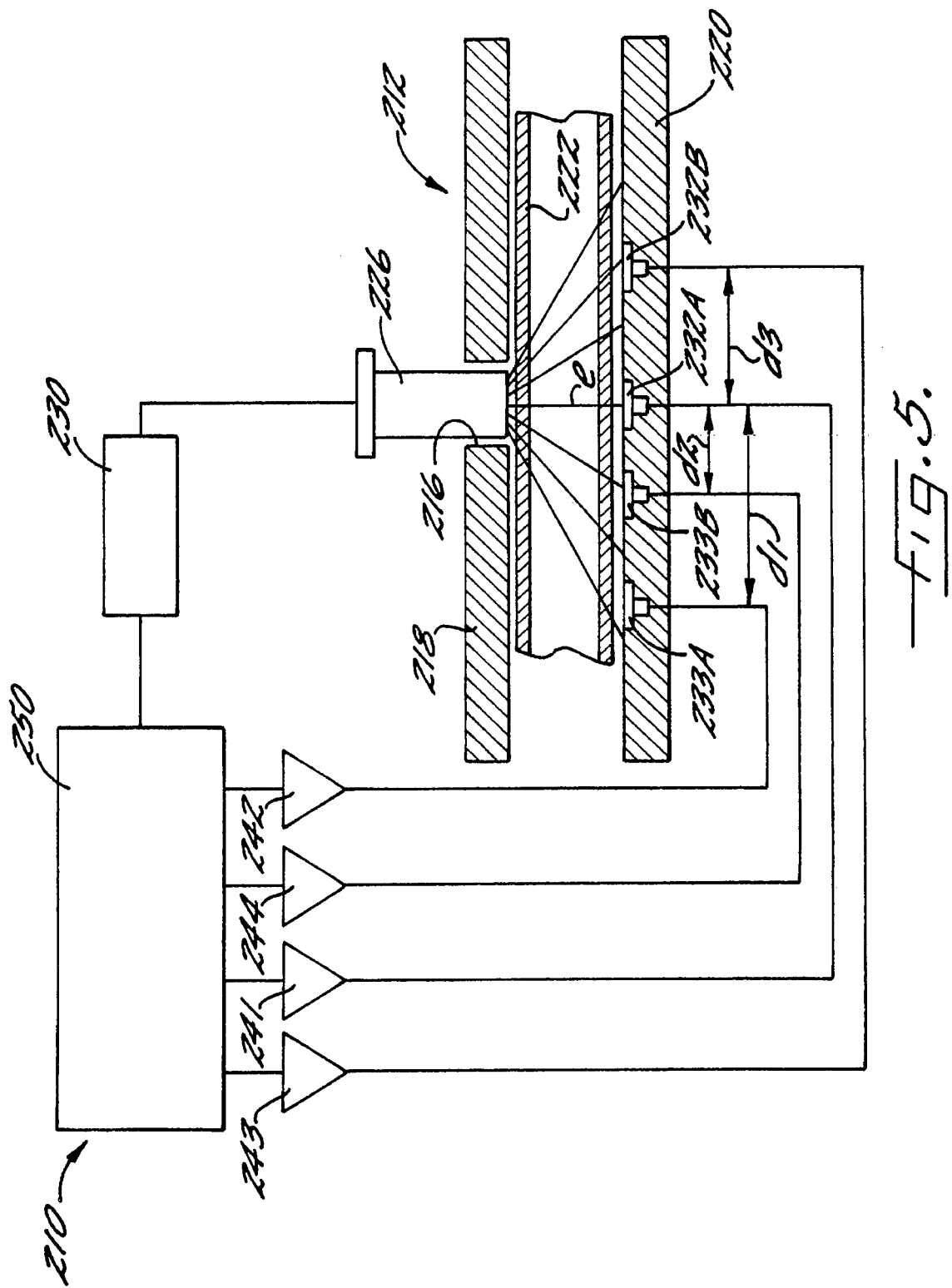
FIG. 5 is a schematic diagram of a third preferred analysis device in accordance with the present invention.

With reference to FIG. 5, a third preferred embodiment of the present invention is shown, in which a single light source is used with four detectors. Corresponding numerals are used in FIG. 5 to indicate parts of device 210 corresponding to device 10, and, for sake of brevity, no description is given of corresponding parts except as otherwise now provided.

In accordance with this embodiment, device 210 includes a flow cell 222 disposed within a housing 212, a light source 226, which is preferably a 815 nm light source, and four detectors 232A,233A,232B,233B. Beneficially, each detector is differently located with respect to the light source to receive different information. The area illuminated by the light source is represented in the Figure.

As in device 110, one detector may be located so as to predominantly be sensitive to directly emerging light emanating from the light source, and no other detector is directly illuminated by the light source. Optical axis "e" of a light beam from the light source projects between detectors 233B,232B, and these detectors are located at a different distance with respect to the optical axis. As shown, detector distance of about 1 cm. Optical axis "e" of the light beam is located a distance d2 of about 0.4 cm from detector 233B (center), and a distance d3 of about 0.6 cm from detector 232B (center).

For sake of brevity, no further written description is made of FIG. 5, insofar as, taking into consideration the foregoing description of devices 10 and 110, the remainder of device 210 is believed to be self-evident to one skilled in the art. Likewise, application of the foregoing equation to device 210 is believed to be self-evident, when it is understood that TH is the signal from through detector 232A, SD is the signal from side detector 233A, NR is the signal from near detector 233B, and FR is the signal from far detector 232B. It will be understood, of course, that further ratios and products may be derived from the data obtained from the four detectors, for instance, the ratio of the through and near detector signals may be obtained; and that equation components may be disregarded as appropriate.

Figure 6:
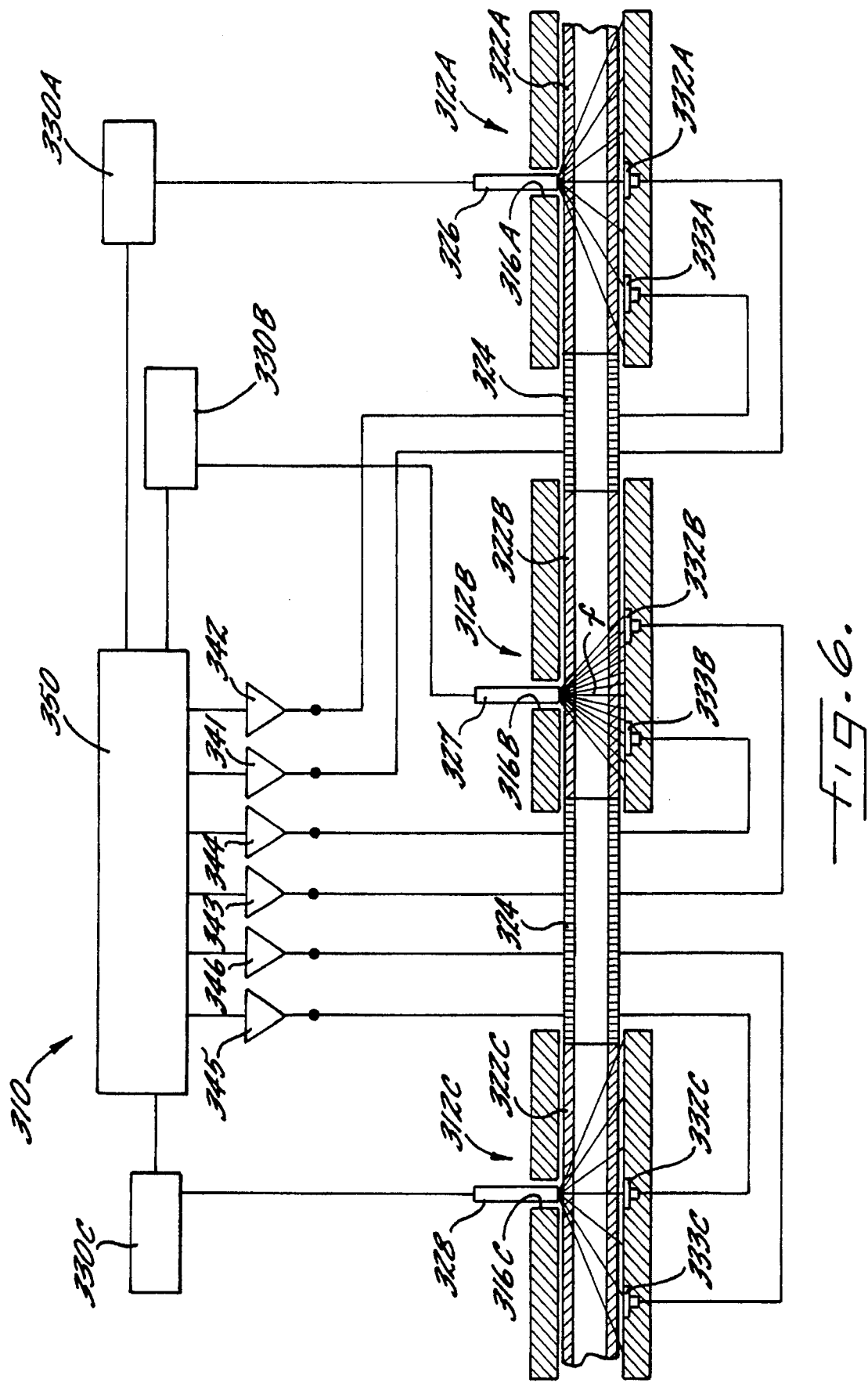
FIG. 6 is a schematic diagram of a fourth preferred analysis device in accordance with the present invention.

With reference to FIG. 6, a fourth preferred embodiment of the present invention is shown, in which three light sources are used, and each light source is followed by a separate set of detectors. Corresponding numerals are used in FIG. 6 to indicate parts of device 310 corresponding to device 110, and, for sake of brevity, no description is given of corresponding parts except as otherwise now provided.

In accordance with this embodiment, device 310 includes flow cells 322A,322B,322C disposed within housings 312A, 312B,312C, extracorporeal circuit tubing 324 connecting the flow cells, means 326,327,328 for generating light beams and detecting means 332A,333A,332B,333B,332C, 333C disposed within the respective housings. Driver 330A drives the first light source, driver 330B drives the second light source, and driver 330C drives the third light source. The areas illuminated by the light sources are represented in the Figure.

As shown, each flow cell has a single light source and a separate set of detectors. Advantageously, the detectors within a set may be spaced apart, center to center, a distance of about 1 cm. Beneficially, at least one detector may be located so as to predominantly be sensitive to directly emerging light. As shown, two detectors may be so located; otherwise, no other detector is directly illuminated by a light source. Optical axis "f" of a light beam from light source 327 projects between detectors 332B,333B. Light source 327 is offset so as to be closer to one detector than the other.

As may be understood, the detectors are located so as to provide four distinct detection locations. Detectors 332C, 333C are suitably similarly disposed as detectors 332A, 333A. Beneficially, when 815 nm, 670 nm and 940 nm light sources are used, detector 332A may be located to be predominantly sensitive to directly emerging light emanating from the 815 nm light source; the 670 light source may be located so that detector 332B is a "far detector" and detector 333B is a "near detector"; and detector 332C may be located to be predominantly sensitive to directly emerging light emanating from the 940 nm light source.

In accordance with this embodiment, advantageously, a first amplification means 341 operatively communicates with detector 332A, a second amplification means 342 operatively communicates with detector 333A, a third amplification means 343 operatively communicates with detector 332B, a fourth amplification means 344 operatively communicates with detector 333B, a fifth amplification means 345 operatively communicates with detector 332C, and a sixth amplification means 346 operatively communicates with detector 333C. Also in accordance with this embodiment, the device suitably includes conventional analog to digital (A/D) converter means and signal processing means 350. Conveniently, A/D converter means 350 includes six channels for separately processing the signals.

With continued reference to device 310, processing of signal information to determine a blood parameter (BP) of interest may be by the use of the following equation which follows intensity and geometry of an emerging light beam, when wavelengths of 815 nm, 670 nm and 940 nm are used in housings 312A,312B,312C, respectively:

$$BP = A\log815TH + B\log815SD + C(\log815TH \times \log815SD) + D(\log815TH/\log815SD) + E\log670NR + F\log670FR + G(\log670NR \times \log670FR) + H(\log670NR/\log670FR) + I\log940TH + J\log940SD + K(\log940TH \times \log940SD) + L(\log940TH/\log940SD) + M,$$

where 815TH is the signal from through detector 332A, 815SD is the signal from side detector 333A, 670NR is the signal from near detector 333B, 670FR is the signal from far detector 332B, 940TH is the signal from through detector 332C, 940SD is the signal from side detector 333C, and A, B, C . . . M are constants. As before, this equation would be the same for other wavelengths except that the equation may specify the other wavelengths used. Also, total intensity could be evaluated by a sum of logs, rather than, as shown, a product of logs; and the determination may not necessarily always require log calculations, and may even use a combination of logs and ordinary numbers.

Here also, evaluation may show that components of the equation either contribute insignificantly or do not contribute positively to the determination, and hence may be disregarded. For determining hematocrit, the following simplified linear equation may be particularly suitable:

$$BP = A815TH + B815SD + E670NR + F670FR + I940TH + J940SD + M.$$

Moreover, the following further simplified equation may be highly useful:

$$BP = B815SD + F670FR + I940TH + M,$$

with a relative weighting based upon degree of importance, being 940TH, 815SD and 670FR in the order given. It will be understood that the constants for a simplified equation would not be the same as the constants for an equation including more components, and that log values may be used.

As indicated, the monitoring devices and method of the present invention may be used on-line with an extracorporeal circuit through which a patient's blood is circulated. However, the inventive concept is equally applicable to analysis of blood in a body part that can be transilluminated. More precisely, the invention may be applied to non-invasive devices (probes). Accordingly, the invention may be embodied in clip-like devices for attachment to body parts which can be transilluminated such as fingers, toes and ear lobes.

In such non-invasive devices, changes in volume and/or emitter-to-detector distance should be minimized. Similarly, in the earlier-described devices, a constant light path between a light source and each detector is beneficial. With respect to the non-invasive devices, a tight fit should be ensured. Rotational movement may be prevented by the use of rubberized, high friction surfaces. Changes in volume and device movement may be minimized by tightening with Velcro® straps.

When used for on-line monitoring, net volume exchange (VE) with or from the circulating vascular volume (VC) at any time (t), may be obtained using hemoglobin as a optically detectable reference with the following equation:

$$VE(t) = VC \cdot (1 - Hbg_0/Hbg(t)),$$

where $Hbg_0$ represents the initial hemoglobin, and $Hbg(t)$ is the concentration of hemoglobin at time (t). Monitoring of volume exchanged is of value in the mobilization of edema because if edema is mobilized into the blood stream, fluid must be removed appropriately to prevent dangerous increases in VC and excessive anemia. In many instances, fluid removal is undertaken in conjunction with acute dialysis, in which case a monitoring device in accordance with the present invention, may be attached to the dialysis circuit. If dialysis is not undertaken, a non-invasive device in accordance with the present invention, may be used.

Applications of the present invention include monitoring of fluid balance with appropriate feedback. When a monitoring device in accordance with the present invention, is placed on an intermittent or continuous dialysis system, proximal to the filtering device, a patient's hemoglobin and the volume exchanged from the patient's blood volume may be continuously monitored and displayed. This information may support a feed-back electronic system to regulate the rate of ultrafiltration and to maintain an adequate and safe circulating blood volume while fluid exchange is induced.

Having described the invention in detail and by reference to preferred embodiments, it will be apparent that modifications and variations are possible without departing from the scope of the invention defined in the appended claims.

I claim:

1. A method for optically determining blood parameters, said method comprising:

a) directing at least one light beam into a patient's blood, and detecting and measuring light emerging from the blood at a plurality of distinct detection locations one of which is predominantly sensitive to directly emerging light;

b) deriving constant values related to said distinct detection locations, based upon data from said detecting and measuring, and data for a selected blood parameter; and c) selecting at least three distinct detection locations from said plurality of distinct detection locations, for later determining said blood parameter.

2. The method of claim 1, further comprising:

d) repeating steps a) and b) to derive revised constant values related to the selected detection locations;

e) thereafter at a later point in time repeating step a); and f) determining said blood parameter at said later point in time, from the data so obtained by step e) and said revised constant values.

3. The method of claim 1, comprising directing a light beam of a first wavelength into said blood, and directing a light beam of a different wavelength into said blood, wherein at least four detection means are used, wherein a first detection means of said at least four detection means is located to be predominantly sensitive to directly emerging light of said first wavelength, wherein a second detection means of said at least four detection means is located for sensitivity to scattered emerging light of said first wavelength, and wherein a third detection means of said at least four detection means is located for sensitivity to scattered emerging light of said second wavelength.

4. The method of claim 1, wherein blood concentration of optically detectable macromolecules is determined.

5. The method of claim 1, wherein a blood parameter selected from hemoglobin concentration, hematocrit, protein concentration, electrolyte concentration and oxygen content is determined.

6. The method of claim 5, wherein hemoglobin is determined, and a change in circulating blood volume is determined from said hemoglobin concentration.

7. The method of claim 1, comprising a calibrating step, comprising directing said light beam into calibrating means for scattering said light beam to a suitable reference geometry; and assigning a selected value to the emerging light sensed at each of said plurality of distinct detection locations.

8. The method of claim 1, wherein said light beam is directed into an extracorporeal circuit containing flowing blood.

9. The method of claim 8, comprising returning said blood to the patient after said measuring and detecting step.

10. A device for optically determining blood parameters, said device comprising first means for generating a first light beam suitable for being directed into a patient's blood; second means for generating a second light beam suitable for being directed into a patient's blood, said first light beam having an optical axis, and said second light beam having an optical axis spaced apart from the optical axis of said first light beam; and first detecting means and second detecting means spaced apart from one another, wherein said first detecting means provides for directly emerging light of said first light beam to be predominantly detected and for scattered emerging light of said second light beam to be detected, wherein said second detecting means provides for scattered emerging light of said first light beam and for scattered emerging light of said second light beam to be detected, and wherein one of said first detecting means and said second detecting means is located relatively closer to said optical axis of said second light beam than the other of said first detecting means and said second detecting means is located.

11. The device of claim 10, wherein said detecting means are light detecting means.

12. The device of claim 10, wherein said first means for generating a light beam, emits a wavelength in the infrared range, and said second means for generating a light beam, emits a visible wavelength.

13. A device for optically determining blood parameters, said device comprising first means for generating a first light beam suitable for being directed into a patient's blood, and a first detecting means for sensing emerging light of said first light beam; second means for generating a second light beam suitable for being directed into a patient's blood, and a second detecting means for sensing emerging light of said second light beam; third means for generating a third light beam suitable for being directed into a patient's blood, and a third detecting means for sensing emerging light of said third light beam; wherein said detecting means are disposed at at least three distinct detection locations with respect to said light beams, and wherein at least one of said detecting means provides for directly emerging light to be predominantly detected.

14. A method for optically determining blood parameters, said method comprising:

a) directing a light beam of a first wavelength into a patient's blood, and thereafter directing a light beam of a different wavelength into the patient's blood;

b) detecting and measuring light emerging from the blood at a plurality of distinct detection locations one of which is predominantly sensitive to directly emerging light;

c) deriving constant values related to said distinct detection locations and said wavelengths, based upon data from said detecting and measuring, and data for a selected blood parameter; and d) selecting at least three distinct detection locations from said plurality of distinct detection locations, for later determining said blood parameter.

15. The method of claim 14, wherein blood concentration of optically detectable macromolecules is determined.

16. The method of claim 14, wherein a blood parameter selected from hemoglobin concentration, hematocrit, protein concentration, electrolyte concentration and oxygen content is determined.

17. The method of claim 14, wherein hemoglobin is determined, and a change in circulating blood volume is determined from said hemoglobin concentration.

18. The method of claim 14, wherein said light beams are directed into an extracorporeal circuit containing flowing blood, comprising returning said blood to the patient after said measuring and detecting.

* * * * *